US007709695B1

(12) United States Patent
Nilsson et al.

(10) Patent No.: US 7,709,695 B1
(45) Date of Patent: May 4, 2010

(54) TRANSGENIC MOUSE EXPRESSING ARCTIC MUTATION E693G

(75) Inventors: Lars Nilsson, Uppsala (SE); Lars Lannfelt, Uppsala (SE); Pär Gellerfors, Lidingö (SE)

(73) Assignee: BioArctic Neuroscience AB, Stockholm (SE)

( * ) Notice: Subject to any disclaimer, the term of this patent is extended or adjusted under 35 U.S.C. 154(b) by 514 days.

(21) Appl. No.: 10/593,639

(22) PCT Filed: Mar. 17, 2005

(86) PCT No.: PCT/SE2005/000383

§ 371 (c)(1),
(2), (4) Date: Dec. 29, 2006

(87) PCT Pub. No.: WO2005/089539

PCT Pub. Date: Sep. 29, 2005

(30) Foreign Application Priority Data

Mar. 22, 2004 (SE) .................................. 0400707

(51) Int. Cl.
*G01N 33/00* (2006.01)
*A01K 67/033* (2006.01)
(52) U.S. Cl. ................................ 800/18; 800/3; 800/12; 800/25
(58) Field of Classification Search ....................... None
See application file for complete search history.

(56) References Cited

FOREIGN PATENT DOCUMENTS

| WO | WO 02/03911 | 1/2002 |
| WO | WO 02/102412 | 12/2002 |
| WO | WO 2004/041213 | 5/2004 |

OTHER PUBLICATIONS

Nilsberth et al. The 'Arctic' APP Mutation (E693G) Cuases Alzheimer's Disease by Enhanced A-Beta Protofibril Formation. Nature Neuroscience. Sep. 2001, vol. 4, pp. 887-893.*
Chishti et al. Early-Onset Amyloid Deposition and Cognitive Deficits in Transgenic Mice Expressing a Double Mutant Form of Amyloid Precursor Protein 695. Journal of Biological Chemistry. 2001, vol. 276, pp. 21562-21570.*
Dudal et al. Inflammation Occurs Early During the A-Beta Deposition Process in TgCRND8 Mice. Neurobiology of Aging. 2004, vol. 25, pp. 861-871.*
Ristevski. Making Better Transgenic Models. Molec. Biotech. 2005, vol. 29, pp. 153-163.*
Echeverria et al. Rat Transgenic Models with a Phenotype of Intracellular A-Beta Accumulation in Hippocampus and Cortex. Journal of Alzheimer's Disease. 2004, vol. 6, pp. 209-219.*
Montoliu. Gene Transfer Strategies in Animal Transgenesis. Cloning and Stem Cells. 2002, vol. 4, pp. 39-46.*
Cai et al., "Release of excess amyloid b protein from a mutant amyloid b protein precursor," *Science*, vol. 259, No. 5094, Jan. 22, 1993, pp. 514-516.

Cairns et al., "BA4 protein deposition in familial Alzheimer's disease with the mutation in codon 717 of the BA4 amyloid precursor protein gene and sporadic Alzheimer's disease," *Neuroscience Letters*, vol. 149, 1993, pp. 137-140.
Chartier-Harlin et al., "Letters to *Nature*: Early-onset Alzheimer's disease caused by mutations at codon 717 of the β-amyloid precursor protein gene," *Nature*, vol. 353, Oct. 31, 1991, pp. 844-846.
Chishti et al., "Early-onset amyloid deposition and cognitive deficits in transgenic mice expressing a double mutant form of amyloid precursor protein 695," *The Journal of Biological Chemistry*, vol. 276, No. 24, Jun. 15, 2001, pp. 21562-21570.
Chui et al., "Transgenic mice with Alzheimer presenilin 1 mutations show accelerated neurodegeneration without amyloid plaque formation," *Nature Medicine*, vol. 5, No. 5, May 1999, pp. 560-564.
Citron et al., "Letters to *Nature*: Mutation of the B-amyloid precursor protein in familial Alzheimer's disease increases B-protein production," *Nature*, vol. 360, Dec. 17, 1992, pp. 672-674.
Corder et al., "Gene dose of apoliprotein E type 4 allele and the risk of Alzheimer's disease in late onset families," *Science*, vol. 261, Aug. 13, 1993, pp. 921-923.
Crowther et al., "Intraneuronal A B, non-amyloid aggregates and neurodegeneration in a drosophila model of Alzheimer's disease," *Neuroscience*, vol. 132, 2005, pp. 123-135.
Demattos et al., "Reports: Brain to plasma amyloid- B efflux: A measure of brain amyloid burden in a mouse model of Alzheimer's disease," *Science*, vol. 295, Mar. 22, 2002, pp. 2264-2267.
Edbauer et al., "Reconstitution of γ-secretase activity," *Nature Cell Biology*, vol. 5, May 2003, pp. 486-488.
Fagan et al., "Human and murine ApoE markedly alters A B metabolism before and after plaque formation in a mouse model of Alzheimer's disease," *Neurobiology of Disease*, vol. 9, 2002 pp. 305-318.
Games et al., "Letters to *Nature*: Alzheimer-type neuropathology in transgenic mice overexpressing V717F β-amyloid precursor protein," *Nature*, vol. 373, Feb. 9, 1995, pp. 523-527.
Glenner et al., "Alzheimer's disease: Initial report of the purification and characterization of a novel cerebrovascular amyloid protein," *Biochemical and Biophysical Research Communications*, vol. 120, No. 3, May 18, 1984, pp. 885-890.
Goate et al., "Letters to *Nature*: Segregation of a missense mutation in the amyloid precursor protein gene with familiar Alzheimer's disease," *Nature*, vol. 349, Feb. 21, 1991, pp. 704-705.
Holcomb et al., "Accelerated Alzheimer-type phenotype in transgenic mice carrying both mutant *amyloid precursor protein and presenilin 1* transgenes," *Nature Medicine*, vol. 4, No. 1, Jan. 1998, pp. 97-100.
Hsiao et al., "Correlative Memory Deficits, Ab Elevation, and amyloid plaques in transgenic mice," *Science*, New Series, vol. 274, No. 5284, Oct. 4, 1996, pp. 99-102.

(Continued)

*Primary Examiner*—Deborah Crouch
(74) *Attorney, Agent, or Firm*—Young & Thompson

(57) ABSTRACT

A transgenic non-human animal expressing at least one transgene including a DNA sequence encoding a heterologous Amyloid Precursor Protein (APP) including at least the Arctic mutation (E693G) and a further AD (Alzheimer's disease) pathogenic mutation or a further transgene affecting AD pathogenesis, which results in increased amounts of intracellular soluble A aggregates, including A peptides. The method of producing the transgenic animal, and methods of screening for therapeutic or diagnostic agents useful in treatment or diagnosis of Alzheimer's disease are also disclosed.

19 Claims, 10 Drawing Sheets

OTHER PUBLICATIONS

Iwata et al., "Clearance of amyloid-β peptide in the brain by adeno-associated viral vector-mediated neprilysin gene transfer," *33rd Annual Meeting of the Society of Neuroscience*, New Orleans, Nov. 8-12, 2003, 2 pp. abstract.

Kang et al., "Letters to *Nature*: The precursor of Alzheimer's disease amyloid A4 protein resembles a cell-surface receptor," *Nature*, vol. 325, Feb. 19, 1987, pp. 733-736.

Klyubin et al., "Soluble arctic amyloid B protein inhibits hippocampal long-term potentiation in vitro," *European Journal of Neuroscience*, vol. 19, 2004, pp. 2839-2846.

Lantos et al., "Familial Alzheimer's disease with the amyloid precursor protein position 717 mutation and sporadic Alzheimer's disease have the same cytoskeletal pathology," *Neuroscience Letters*, vol. 137, 1992, pp. 221-224.

Lashuel et al., "Mixtures of wild-type and a pathogenic (E22G) form of A B40 in vitro accumulate protofibrils, including amyloid pores," *Journal of Molecular Biology*, 2003, vol. 332, pp. 795-808.

Li et al., "Intracellular accumulation of detergent-soluble amyloidogenic A B fragment of Alzheimer's disease precursor protein in the hippocampus of aged transgenic mice," *Journal of Neurobiology*, 1999, pp. 2479-2487.

Lorenzo et al., "B-amyloid neurotoxicity requires fibril formation and is inhibited by Congo red," *Proceedings of the National Academy of Science USA*, vol. 91, Dec. 1994, pp. 12243-12247.

Masters et al., "Amyloid plaque core protein in Alzheimer disease and Down Syndrome," *Proceedings of the National Academy of Sciences USA*, vol. 82, Jun. 1985, pp. 4245-4249.

Mullan et al., "A pathogenic mutation for probable Alzheimer's disease in the APP gene at the N-terminus of β-amyloid," *Nature Genetics*, vol. 1, Aug. 1992, pp. 345-347.

Murrell et al., "A mutation in the amyloid precursor protein associated with hereditary Alzheimer's disease," *Science*, vol. 254, No. 5028, Oct. 4, 1991, pp. 97-99.

Naslund et al., "Correlation between elevated levels of amyloid β-peptide in the brain and cognitive decline," *Journal of the American Medical Association*, vol. 283, No. 12, Mar. 22-29, 2000, pp. 1571-1577.

Nilsberth et al., "The 'Arctic' APP mutation (E6930) causes Alzheimer's disease by enhanced Aβ protofibril formation," *Neuroscience*, vol. 4, No. 9, Sep. 2001, pp. 887-893.

Nilsson et al., "α-1-Antichymotrypsin promotes β-sheet amyloid plaque deposition in a transgenic mouse model of Alzheimer's disease," *The Journal of Neurosciences*, vol. 21, No. 5, Mar. 1, 2001, pp. 1444-1451.

Pike et al., "In vitro aging of β-amyloid protein causes peptide aggregation and neurotoxicity," *Brain Research*, vol. 563, 1991, pp. 311-314.

Roher et al., "The human amyloid-β precursor protein$_{770}$ mutation V717F generates peptides longer than amyloid-β-(40-42) and flocculent amyloid aggregates," *The Journal of Biological Chemistry*, vol. 279, No. 7, Feb. 13, 2004, pp. 5829-5836.

Scheuner et al., "Secreted amyloid β-protein similar to that in the senile plaques of Alzheimer's disease is increased in vivo by the presenilin 1 and 2 and *APP* mutations linked to familial Alzheimer's disease," *Nature Medicine*, vol. 2, No. 8, Aug. 1996, pp. 864-870.

Selkoe, "Cell biology of the β-amyloid protein precursor and the mechanism of Alzheimer's disease," *Annual Review of Cell Biology*, vol. 10, 1994, pp. 373-403.

Selkoe, "Normal and abnormal biology of the β-amyloid precursor protein," *Annual Review of Neuroscience*, vol. 17, 1994, pp. 489-517.

Stenh et al., "The Arctic mutation interferes with processing of the amyloid protein precursor," *NeuroReport*, vol. 13, No. 15, Oct. 28, 2002, pp. 1857-1860.

Strittmatter et al., "Apolipoprotein E: High-avidity binding to β-amyloid and increased frequency of Type 4 allele in late-onset familial Alzheimer disease," *Proceedings of the National Academy of Science USA*, vol. 90, Mar. 1993, pp. 1977-1981.

Sturchler-Pierrat et al., "Two amyloid precursor protein transgenic mouse models with Alzheimer disease-like pathology," *Proceedings of the National Academy of Science USA*, Neurobiology, vol. 94, Nov. 1997, pp. 13287-13292.

Suzuki et al., "An increased percentage of long amyloid b protein secreted by familial amyloid b protein precursor (baPP$_(717)$) Mutants," *Science*, vol. 264, No. 5163, May 27, 1994, pp. 1336-1340.

Walsh et al., "Letters to Nature: Naturally secreted oligomers of amyloid β protein potently inhibit hippocampal long-term potentiation in vivo," *Nature*, vol. 416, Apr. 4, 2002, pp. 535-539.

\* cited by examiner

Thy-SwedishArcticAPP founder lines

Fig. 3
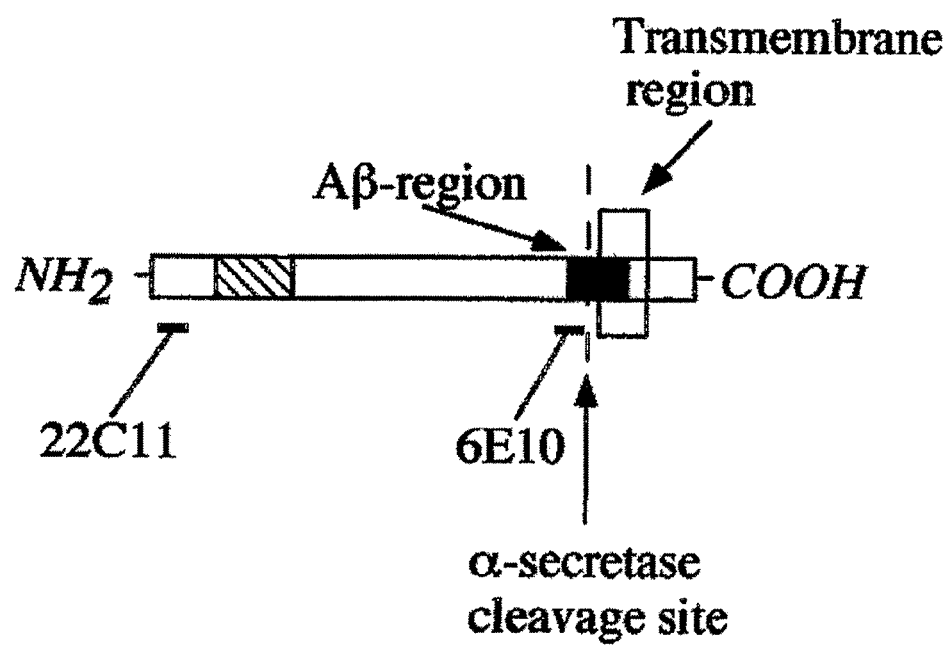

Fig. 10
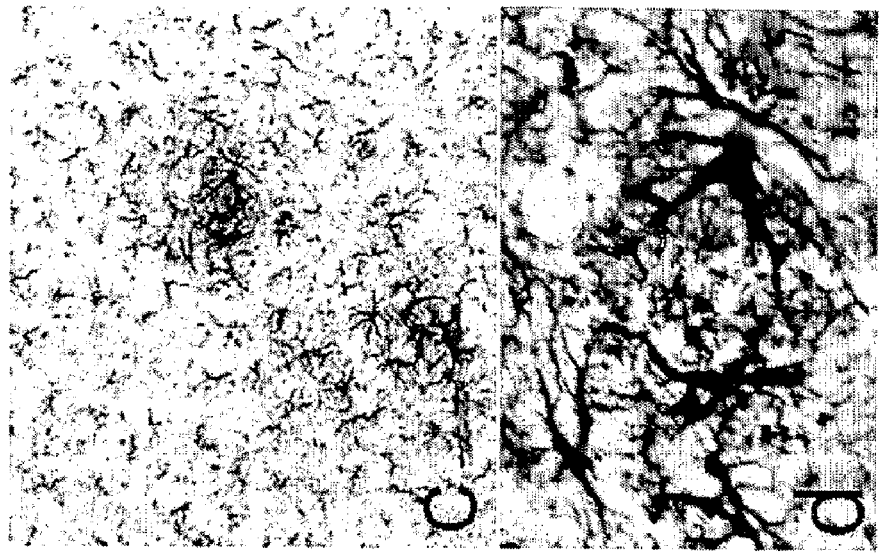
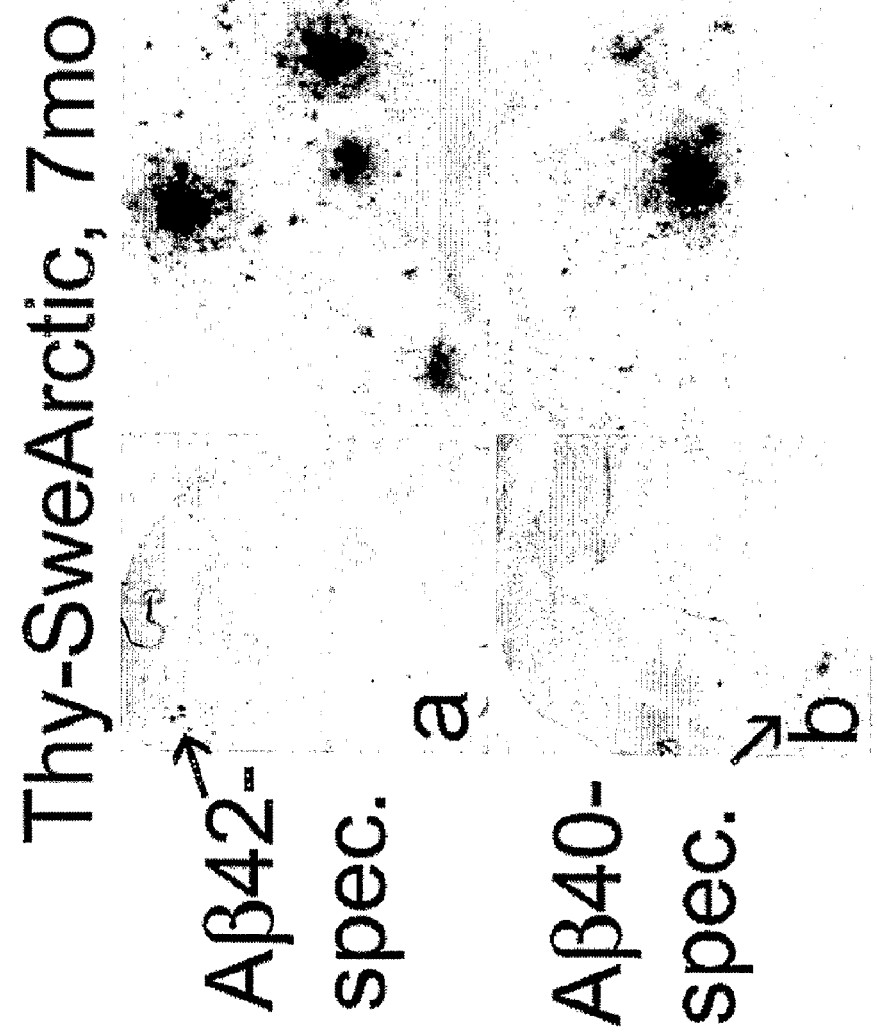

TRANSGENIC MOUSE EXPRESSING ARCTIC MUTATION E693G

FIELD OF INVENTION

The present invention relates to a transgenic animal model of Alzheimer's disease and related neurological disorders. The present invention also relates to method of producing said transgenic animal, and to methods of screening for therapeutic or diagnostic agents useful in treatment or diagnosis of Alzheimer's disease.

BACKGROUND OF THE INVENTION

Alzheimer's disease (AD) is a progressive and irreversible neurodegenerative disorder causing cognitive, memory and behavioral impairments. It is the most common cause of dementia in the elderly population affecting roughly 5% of the population above 65 years and 20% above 80 years of age. AD is characterized by an insidious onset and progressive deterioration in multiple cognitive functions. The neuropathology involves both extracellular and intracellular argyrophillic proteineous deposits. The extracellular deposits, referred to as neuritic plaques, mainly consist in amyloid-beta (Aβ) peptides surrounded by dystrophic neurites (swollen, distorted neuronal processes). The Aβ peptides within these extracellular deposits are fibrillar in their character with a β-pleated sheet structure. Aβ in these deposits can be stained with certain dyes e.g. Congo Red and display a fibrillar ultrastructure. These characteristics, adopted by Aβ peptides in its fibrillar structure of neuritic plaques, are the definition of the generic term amyloid. Frequent neuritic plaques and neurofibrillary tangles deposits in the brain are diagnostic criteria for AD, as carried out when the patient has died. AD brains also display macroscopic brain atrophy, nerve cell loss, local inflammation (microgliosis and astrocytosis) and often congophilic amyloid angiopathy (CAA) in cerebral vessel walls.

Two forms of Aβ peptides, Aβ40 and Aβ42, are the dominant species of AD neuritic plaques (Masters et. al., 1985), while Aβ40 is the prominent species in cerebrovascular amyloid associated with AD (Glenner and Wong, 1984). Enzymatic activities allow these Aβ to be continuously formed from a larger protein called the amyloid precursor protein (APP) in both healthy and AD afflicted subjects in all cells of the body. Two major APP processing events β- and γ-secretase activities enables Aβ-peptide production through enzymatic cleavage, while a third one called α-secretase activities prevents Aβ-peptide by cleavage inside the Aβ-peptide sequence (reviewed in Selkoe, 1994; U.S. Pat. No. 5,604,102). The Aβ42 is forty two amino acid long peptide i.e. two amino acids longer at the C-terminus, as compared to Aβ40. The Aβ42 peptide is more hydrophobic, and does more easily aggregate into larger structures of Aβ peptides such as Aβ dimers, Aβ tetramers, Aβ oligomers, Aβ protofibrils or Aβ fibrils. Aβ fibrils are hydrophobic and insoluble, while the other structures are all less hydrophobic and soluble. All these higher molecular structures of Aβ peptides are individually defined based on their biophysical and structural appearance e.g. in electron microscopy, and their biochemical characteristics e.g. by analysis with size-exclusion chromatography/western blot. These Aβ peptides, particularly Aβ42, will gradually assemble into a various higher molecular structures of Aβ during the life span. AD, which is a strongly age-dependent disorder, will occur earlier in life if this assembly process occurs more rapidly in the brain of that individual. This is the core of the "amyloid cascade hypothesis" of AD which claims that APP processing, the Aβ42 levels and their assembly into higher molecular structures are central cause of all AD pathogenesis. All other neuropathology of AD brain and the symptoms of AD such as dementia are somehow caused by Aβ peptides or assembly forms thereof. The strongest evidence for the "amyloid cascade hypothesis" comes from genetic studies of individuals in families afflicted by early onset of familial AD as a dominant trait. These studies have revealed that rare mutations in the APP gene are sufficient to generate severe forms of AD. The mutations are clustered in and around Val 717 slightly downstream of the Aβ1-42 C-terminus (Goate et al., 1991, Chartier-Harlan, et al., 1991, Murrell, et al., 1991) and a unique double mutation (670-671) immediately upstream of the Aβ N-terminus in a Swedish family (Mullan, et al., 1992; U.S. Pat. No. 5,795,963). The APP mutations, which frames the Aβ peptide sequence, were later found to either increase both Aβ40 and Aβ42 production (the "Swedish" mutation; Citron, et al., 1992, Cai et al., 1993), or to increase the ratio of Aβ42/Aβ40 production and also to generate Aβ peptides that are C-terminally extended to incorporate the pathogenic mutation in the Aβ peptide e.g. Aβ50 (the "717"-mutations are at position 46; Suzuki et al., 1994; Roher et al., 2003). Thus the "717" mutations, in addition to wild-type Aβ40 and wild-type Aβ42, also generate London Aβ peptides (V717I) and Indiana Aβ peptides (V7171F, Aβ46 and longer forms of Aβ) which rapidly forms Aβ fibrils. In contrast, the Swedish mutation only generates increased levels of wild-type Aβ40 and Aβ42 peptides. Early onset familial AD is more often caused by mutations in presenilin 1 (on chromosome 14; U.S. Pat. No. 5,986,054; U.S. Pat. No. 5,840,540; U.S. Pat. No. 5,449,604) and in some cases by mutations in presenilin 2 (chromosome 1). Presenilin 1 and presenilin 2 are both polytopic transmembrane proteins that, together with three other proteins nicastrin, aph1 and pen-2, constitute the necessary functional core of the γ-secretase complex that enables Aβ-peptide formation through enzymatic cleavage of APP (Edbauer et al., 2003). All AD pathogenic mutations in presenilin 1 and presenilin 2 proteins significantly increase Aβ 1-42 overproduction (Schuener et al., 1996). Apolipoprotein E (ApoE) is, besides age, the most important risk factor for late-onset AD. There are three variants of the ApoE protein in humans, due to single amino acid substitutions in the ApoE protein. The ApoE4 variant confers increased risk of AD, while the ApoE2 variant is protective as compared to the predominant ApoE3 variant (Strittmatter et al., 1993; Corder et al., 1993). These protein changes are not deterministic, but confer enhanced or decreased susceptibility to develop AD in a population. The ability of the ApoE variants to facilitate amyloid deposition in APP transgenic mice models of AD is greatest for ApoE4, intermediate for ApoE3 and lowest for ApoE2, suggesting that the AD pathogenic mechanism of ApoE is to enhance Aβ-peptide assembly and/or amyloid deposition (Fagan et al., 2002). Other proteins such as $\alpha_1$-antichymotrypsin (Nilsson et al., 2001) and ApoJ/clusterin (DeMattos et al., 2002) also enhance Aβ-peptide assembly and/or amyloid deposition in APP transgenic mice, similar to ApoE. Neprilysin (NEP) and insulin-degrading enzyme (IDE) degrade Aβ peptides and are likely implicated in AD. However, none of these proteins has been proven to be involved in AD by human genetics. A key issue in future AD research is to better understand how enhanced levels Aβ or aggregates thereof cause dementia and functional loss in AD patients. It has been a long-standing belief that the insoluble amyloid fibrils, the main component of the neuritic plaque, are the pathogenic species in AD brain. High concentrations of Aβ fibrils have been shown to be cytotoxic in cell culture models of nerve cells in the brain (Pike et al., 1991; Lorenzo and Yankner et al., 1994). However, the hypothesis of the amyloid fibril as the main neurotoxic species is inconsistent with the poor correlation between neuritic plaque density and AD dementia score and also with the modest signs of neurodegeneration in current APP transgenic mice. Soluble neurotoxic Aβ-intermediate species and their appropriate subcellular site of formation and distribution could be the missing link that will better explain the amyloid hypothesis. This idea has gained support from recent discovery of the Arctic (E693) APP mutation, which causes early-onset AD (W00203911; Nilsberth et al., 2001). The mutation is located inside the Aβ peptide sequence. Mutation carriers will thereby generate variants of Aβ peptides e.g. Arctic Aβ40 and Arctic Aβ42. Both Arctic Aβ40 and Arctic Aβ42 will much more easily assemble into higher molecular structures of Aβ peptides that are soluble and not fibrillar in their structure, particularly Aβ protofibrils named LSAP (Large soluble amyloid protofibrils). Thus the pathogenic mechanism of the Arctic mutation differs from other APP, PS1 and PS2 mutations and suggests that the soluble higher molecular structures of Aβ peptides e.g. Aβ protofibrils is the cause of AD. It has recently been demonstrated that soluble oligomeric Aβ peptides such as Aβ protofibrils impair long-term potentiation (LTP), a measure of synaptic plasticity that is though to reflect memory formation in the hippocampus (Walsh et al., 2001). Furthermore that oligomeric Arctic Aβ peptides display much more profound inhibitory effect than wt Aβ on LTP in the brain, likely due to their strong propensity to form Aβ protofibrils (Klyubin et al., 2003).

An animal model of AD with the features of the human disease is much needed to better understand AD pathogenesis and to evaluate the efficacy of new therapeutic agents. The ideal animal model of AD should generate the complete neuropathology of AD and the clinical phenotype e.g. progressive memory and cognitive dysfunctions. Major progress in this direction has been accomplished using transgenic overexpression of APP harboring AD pathogenic mutations. Current APP transgenic models of AD display important features of AD pathogenesis such as age-dependent and region-specific formation of both diffuse and neuritic plaques in the brain. The amyloid pathology is associated with hyperphosphorylated tau, local inflammation (microgliosis and astrocytosis) and to a variable extent with congophilic amyloid angiopathy (CAA). These models have been generated by very high transgene expression of human APP, particularly in nerve cells of the brain. The transgenes always carries an AD pathogenic mutation. Thus a "717"-APP-mutation (V717F; Games et al. 1995; US2002104104; U.S. Pat. No. 5,720,936; U.S. Pat. No. 5,811,633) or the "Swedish" mutation (KM670/671NL; Hsiao et al., 1996; Sturchler-Pierrat et al., 1997; WO 09803644; US2002049988; U.S. Pat. No. 6,245,964; U.S. Pat. No. 5,850,003; U.S. Pat. No. 5,877,399; U.S. Pat. No. 5,777,194) have been used. Double transgenic mice containing both mutant APP and mutant presenilin-1 transgenes develop accelerated amyloid plaques formation, but the animals still display modest mental impairment and still fail to display NFTs, nerve cell and brain atrophy (Holcomb et al., 1998; U.S. Pat. No. 5,898,094; US2003131364). Furthermore the current APP transgenic models likely have low levels of soluble intermediates in the Aβ fibrillization process such as Aβ protofibrils, which might be of great importance for AD pathogenesis. Several AD pathogenic mutations have previously been combined in one single transgene e.g. the "Swedish" mutation (KM670/671NL) and the "717"-APP-mutation (Indiana, V717F) have been used to enhance and increase formation of fibrillar Aβ peptides and neuritic plaque formation (Janus et al., 2001). Similarly the "Swedish" (KM670/671NL), the "Arctic" (E693G) and a "717"-APP-mutation (London, V717I) have been combined and used in an attempt to generate earlier and increased plaque formation (Teppner et al., 2003), like those of Swedish+Indiana APP transgenic models (Janus et al., 2001), since the London Aβ peptides will strongly facilitate Aβ fibril formation (Teppner et al., 2003; Roher et al., 2003). The unique characteristics of Arctic Aβ40 and Arctic A42 to form an abundance of stable protofibrils have been demonstrated (Nilsberth et al., 2001; Lashuel et al., 2003). The marked difference in pathology in human AD brain between carriers of the London APP mutation (Lantos et al., 1992; Cairns et al., 1993) and Arctic APP mutation reinforce the distinction in the chemical characteristics of London Aβ peptides and Arctic Aβ peptides for neuropathology.

The following references are presently found to be most relevant:

Stenh C. et al. disclose in "Metabolic consequences of the arctic (E693G) APP alzheimer mutation", Society for Neuroscience. Abstract Viewer and Itenary Planner 2002, $32^{nd}$ Annual Meeting of the Society for Neuroscience, Nov. 2-7, 2002, Abstract No. 296.6 and in Neuroreport 13, 1857-60 (2002) a transfected tumorigenic cell-line harboring APP cDNA with both the "Swedish" (KM670/671NL) and "Arctic" (E693G) mutations.

Hsiao et al., Science 274, 99-102 (1996) disclose a transgenic mouse harboring the "Swedish" (KM670/671NL) alone.

Mullan et al., Nature Genet. 1, 345-347 (1992) discloses the dominant inheritance of the "Swedish" (KM670/671NL) in a family with Alzheimer's disease.

Nilsberth et al., Nat. Neurosci. 4, 887-893 (2001) discloses the dominant inheritance of the "Arctic" (E693G) in a family with Alzheimer's disease.

Teppner et al., $6^{th}$ Internat. Conf. AD/PD, Seville, Spain, board no 52 (2003), discloses a preliminary attempt to generate a transgenic mouse harboring the "Swedish" (KM670/671NL), "Arctic" (E693G) and "London" (V717I) mutations. No pathology is described.

Roher et al., J Biol Chem. 279(7): 5829-36 (2004), discloses that Aβ peptides extend beyond amino acid 42, e.g. Aβ 1-46 and Aβ1-50, in Alzheimer brain tissue from patient carrying a "London"-type mutation (V717F).

Kang et al., Nature 325, 733-6 (1987) describes the cloning of human APP695 cDNA.

SUMMARY OF THE INVENTION

In view of the shortcomings of prior art models, the object of the invention is to provide a transgenic animal model that displays early phenotypes of Alzheimer's disease (AD) pathology that can be quantified. This would allow a more rapid and cost-efficient screening of pharmacological agents in the pharmaceutical and biotech industry.

The present invention solves this problem by the provision of an animal model for AD and related neurological disorders having pathologies of enhanced Aβ-40 and/or Aβ-42 Arctic peptides and Aβ Arctic protofibril production and an early soluble oligomeric and protofibrillar Aβ Arctic peptide-driven pathology, including Aβ aggregation inside neurons of the brain.

The Aβ-immunopositive intraneuronal staining (punctate and strong) was resistant to pretreatment with concentrated formic acid, which is a typical characteristic of amyloid, i.e. Aβ aggregates with a β-sheet structure (protofibrils), and was localized to the pyramidal cell layer of CA1 in the hippocampus and in scattered neurons of the lower lamina in the cerebral cortex as well as other neurons in the brain.

According to one aspect, the present invention relates to a new AD transgenic animal (non-human), such as a rodent, more preferably a murine animal and most preferably a mouse, that exhibits early and enhanced intracellular Aβ aggregation, which can be reliably measured. This intracellular Aβ aggregation occurs prior to and gradually increase in amount before the onset of extracellular plaque formation. The early and enhanced soluble intraneuronal Aβ aggregation is a pathological AD phenotype that goes beyond previously described APP transgenic mouse models. This AD phenotype is present in the animal model according to the present invention much earlier than in any AD marker found in previous animal models.

The invention provides a means for identification of agents that interfere, delay or inhibit the Alzheimer disease process at an early stage. Such agents would be of significant clinical importance for treatment of early stage Alzheimer's disease or prevention of its manifestation. The provision of the animal model according to the present invention can greatly shorten the time required for screening for such agents.

Thus the measurement of the extent of intracellular Aβ aggregation allows one to predict the later extracellular Aβ deposition well in advance. This prediction can be made as early as 1-2 months into the development of AD neuropathology. With prior art techniques, this is possible only after 15 months. The present invention can thus be used to more rapidly and cost-efficiently screen for agents that are able to prevent, inhibit and reverse AD neuropathology at an earlier stage.

The transgenic mouse model provided by the invention also display reduced brain weight, which suggests atrophic changes in the brain as is normally observed in human brain afflicted by AD pathogenesis.

According to a basic embodiment, the transgenic animal expresses at least one transgene comprising a DNA sequence encoding a heterologous Amyloid Precursor Protein (APP) comprising at least the Arctic mutation (E693G) and a further mutation which increases the intracellular levels of Aβx peptides.

The present invention includes the introduction of any of the APP transgenes (of wild-type or containing pathogenic AD mutations), that are mentioned in the specification, into the endogenous APP alleles.

According to another embodiment, the transgene comprising the Arctic mutation (E693G) is combined with a further transgene affecting AD pathogenesis which increases the intracellular levels of Aβ-40 and Aβ-42 peptides in the tissues of said transgenic animals. Said further transgene is for example a human presenilin-1 and/or presenilin-2 transgene harboring at least one AD pathogenic mutation. Said further transgene may also be a transgene harboring a DNA sequence encoding the apolipoprotein E, apolipoprotein J (clusterin), α$_1$-antichymotrypsin (ACT) or fragments thereof.

According to another embodiment, the transgenic animal according to present invention further comprises a homologously integrated targeting construct for at least one of the neprilysin or insulin-degrading enzyme (IDE) genes, which disrupts these genes through gene ablation (knock-out) and enhances Aβ-40 and/or Aβ-42 Arctic peptide production.

According to a presently preferred embodiment, the transgenic animal is a mouse harboring a transgene encoding amyloid precursor protein (APP) consisting of the Arctic mutation (E693G) and the Swedish mutation KM670/671NL), and no further APP mutations.

According to another aspect, the present invention also relates to a method of preparing said transgenic animal.

According to another aspect, the present invention also relates to a method of a screening, wherein the transgenic animal is used for screening for agents useful for treating, preventing or inhibiting Alzheimer's disease.

According to another aspect, the present invention also relates to a method of a screening, wherein the transgenic animal is used for screening for diagnostic agents for Alzheimer's disease.

The present invention provides a model for AD and related neurological disorders having pathologies of enhanced Aβ protofibril formation and intraneuronal Aβ peptide aggregation.

The transgenic animals and progeny thereof, typically producing the Arctic Aβ peptides in brain tissue, can be used as a model for a variety of diseases and for drug screening, testing various compounds, evaluation of diagnostic markers as well as other applications.

DESCRIPTION OF THE DRAWINGS

FIG. 3: Graph depicting the APP protein with the kunitz domain (hatched) which enables alternative splicing of APP. The Aβ peptides domain (black) resides partly inside the transmembrane domain. The locations of the epitopes of the APP antibodies used in the experiment are indicated. In the APP770 protein isoform the epitopes are located between aa 66-81 (22C11) and aa 672-687 (6E10). The 22C11 antibody detects both human and endogenous murine APP, while the 6E10 antibody detects only human APP. Western blot showing threefold relative overexpression of APP in brain of Thy-SwedishArctic-APP transgenic mouse, founder line B. Coomassie staining ("Cooma.") is a measure of total protein loaded onto the gel (A). The presence of human APP and Arctic Aβ peptides in brain of Thy-SwedishArctic-APP transgenic mouse, founder line B ("B") and absence in brain of nontransgenic mouse ("ntr") (B) was verified by staining with 6E10 antibody. As said antibody only detects the presence of human APP, the functionality of the transgene is thus verified.

FIG. 10: Extracellular senile plaques in the hippocampus of a Thy-SwedishArcticAPP transgenic mouse at 7 months of age. The Aβ-immunoreactivity was observed with two different antibodies that were specific for the short amino acid fragments in the C-terminal ends of Aβ42 (a) and Aβ40 (b) and thus do not detect APP or APP-fragments (Näslund et al., 2000). The Aβ-immunoreactivity was resistant to and enhanced by pretreatment with concentrated formic acid. The arrows points to Aβ-immunoreactive deposits which are displayed at higher magnification (images between a and b). Combined Congo Red and GFAP-immunostaining shows robust astrogliosis surrounding a compact amyloid plaque (c), which displays classical gold-green birefringence in polarized light (d).

DETAILED DESCRIPTION OF THE INVENTION

Figure 1:
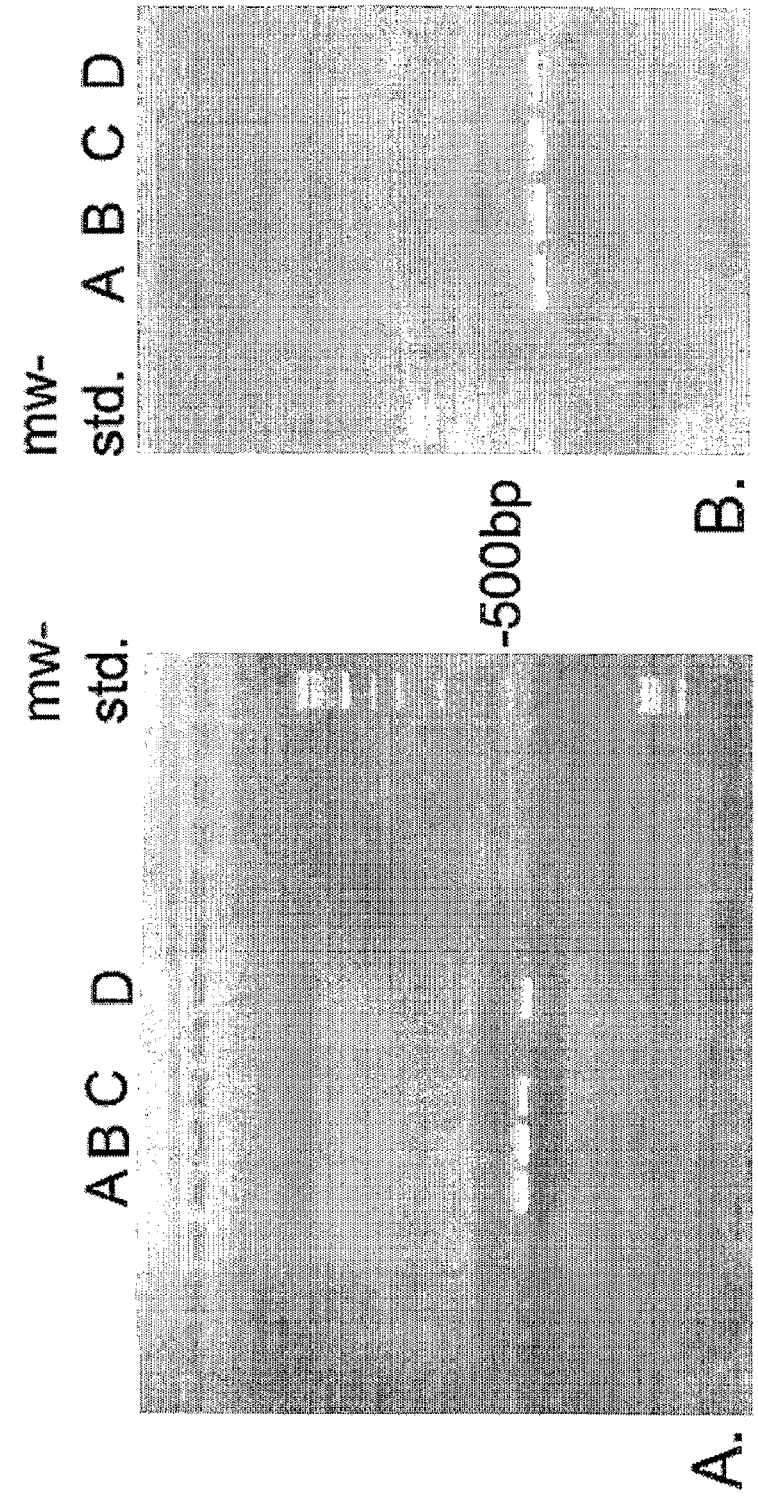
FIG. 1: Ethidium bromide-stained DNA gel showing the presence of positive PCR-signal of DNA-fragments having a length of 428 bp with the upstream (A) primer pair and 441 bp with the downstream (B) primer pair. Genomic DNA from different founder mice have been analyzed and PCR-positive Thy-SwedishArcticAPP founders have been assigned founder line numbers A, B, C and D, as denoted above the gels. DNA molecular weight standard ("mw-std.") shows the lengths of various predefined DNA-fragments. The two primer pairs frames the whole coding region of transgene APP and the basal promoter of the Thy-1 promoter.

The transgenes according to the present invention comprise a polynucleotide sequence, more specifically a heterologous APP polypeptide comprising the herein described mutations, and are operably linked to a transcription promoter capable of producing expression of the heterologous APP polypeptide in the transgenic animal.

Said promoter can be constitutive or inducible, and can affect the expression of a polynucleotide in a general or tissue-specific manner. Tissue-specific promoters include, without limitation, neuron specific enolase (NSE) promoter, neurofilament light chain (NF-L) and neurofilament heavy chain (NF—H) promoter, prion protein (PrP) promoter, tyrosine hydroxylase promoter, platelet-derived growth factor (PDGF) promoter, thy1-glycoprotein promoter, β-actin promoter, ubiquitin promoter, simian virus 40 (SV40) promoter, and gene-specific promoters such as the APP promoter.

The amyloid precursor proteins (APP) comprise a group of ubiquitously expressed transmembrane glycoproteins whose heterogeneity arises from both alternative splicing and post-translational processing [Selkoe, D. J. (1994) NCBI accession nr P05067, SEQ ID NO: 1]. Apart from the 751- and 770-residue splice forms which are highly expressed in non-neuronal cells throughout the body, neurons most abundantly express the 695-residue isoform. All isoforms are the precursors of various metabolites that result from different proteolytic cleavage induced by physiological or pathological conditions. The APP itself, as used according to the principles of this invention, can be any of the alternative splice forms of this molecule and may be used either as a glycosylated or non-glycosylated form.

In a further embodiment, the transgene comprising the Arctic mutation is combined with a further transgene that enhance Aβ-40 and/or Aβ-42 Arctic peptide production. Said increase may be due to increased production or impaired clearance of Aβ peptides in soluble form.

Such a further transgene, is for example a transgene encoding a heterologous presenilin-1 or presenilin-2 harboring AD pathogenic mutations, which further transgene increases the production of Aβ-40 and/or Aβ-42 Arctic peptide levels by γ-secretase cleavage and thereby generate a similar phenotype as that described for the transgene containing the Arctic and Swedish mutations, i.e. early and enhanced intracellular Aβ aggregation. The AD pathogenic mutations are known in the art and may e.g. be selected from those disclosed on: http://www.alzforum.org/res/com/mut/pre/table1.asp (Presenilin-1) and http://www.alzforum.org/res/com/mut/pre/table2.asp (Presenilin-2), which at the filing of the present application were:

Presenilin-1 mutations

A79V
V82L
Leu85Pro
Cys92Ser
V94M
V96F
F105L
Y115C
Y115H
T116N
P117L
P117R
E120D
E120D2
E120K
E123K
N135D
M139I
M139T
M139V
I143F
I143M
I143T
M146I
M146L
M146V
T147I
H163R
H163Y
W165C
S169L
S169P
L171P
L173W
Leu174Met
G183V
E184D
G209V
I213F
I213T
L219F
L219P
Q222H
L226R
A231T
A231V
M233L
M233T
L235P
F237I
A246E
L250S
Y256S
A260V
V261F (Spastic paraparesis)
L262F
C263R
P264L
P267S
R269G -continued R269H
E273A
R278T
E280A
E280G
L282R
A285V
L286V
S290C
S290C2
S290C3
G378E
G384A
S390I
L392V
N405S
A409T
C410Y
L424R
A426P
P436Q
P436S Presenilin-2 mutations R62H
T122P
Ser130Leu
N141I
V148I
Q228L
M239I
M239V In a further embodiment, the further transgene overexpresses apolipoprotein E, apolipoprotein J (clusterin) or α$_1$-antichymotrypsin (ACT) to enhance the fibrillization process of Aβ-40 and/or Aβ-42 Arctic peptides and/or Aβ protofibrils and thereby generate a similar phenotype, i.e. early and enhanced intracellular Aβ aggregation.

In a further embodiment, the animal comprises a targeting construct homologously integrated into an endogenous chromosomal location so as to enhance Aβ-40 and/or Aβ-42 Arctic peptide levels by impaired clearance e.g. through gene ablation (knock-out) of neprilysin and/or insulin-degrading enzyme (IDE) genes in tissues of such transgenic animal harboring the Arctic mutation (E693G) and thereby generate a similar phenotype as that described in the invention i.e. early and enhanced intracellular Aβ aggregation.

Prior to transfection, said further transgenes are crossed with the transgene comprising the Arctic mutation.

The invention further provides transgenic animals, preferably a mouse, which harbors at least one copy of a transgene or targeting construct of the invention, either homologously or non-homologously integrated into an endogenous chromosomal location so as to produce Arctic Aβ peptides. Such transgenic animals are usually produced by introducing the transgene or targeting construct into a fertilized egg or embryonic stem (ES) cell, typically by microinjection, electroporation, lipofection, or biolistics.

The transgenic animals according to the present invention have at least one inactivated endogenous APP allele, are preferably homozygous for inactivated APP alleles, and are substantially incapable of directing the efficient expression of endogenous (i.e., wild-type) APP.

In a preferred embodiment, a transgenic mouse is homozygous for inactivated endogenous APP alleles and substantially incapable of producing murine APP encoded by a endogenous (i.e., naturally-occurring) APP gene. Such a transgenic mouse, having inactivated endogenous APP genes, is a preferred host recipient for a transgene encoding a heterologous APP polypeptide, preferably a human Arctic mutation and the Swedish APP mutation (KM670/671NL) (APP770 numbering) to enhance both Aβ-40 and Aβ-42 Arctic peptide production.

Said Swedish mutation may be replaced with similar mutations such as KM670/671DL, KM670/671DF, KM670/671DY, KM670/671EL, KM670/671EF, M670/671EY, KM670/671NY, KM670/671NF, KM670/671KL (APP770 numbering).

However, the Swedish mutation (KM670/671NL) is presently the mutation that is most preferably combined with the Arctic mutation.

Such a transgenic mouse, having inactivated endogenous APP genes, is also a preferred host recipient for a transgene encoding a heterologous APP polypeptide comprising a human Arctic mutation together with further transgene that enhance Aβ-40 and/or Aβ-42 peptide production, e.g. a further transgene encoding a heterologous presenilin-1 or presenilin-2 harboring AD pathogenic mutations. Such heterologous transgenes may be integrated by homologous recombination or gene conversion into a presenilin-1 or presenilin-2 gene locus, thereby effecting simultaneous knockout of the endogenous presenilin-1 or presenilin-2 gene (or segment thereof) and replacement with the human presenilin-1 or presenilin-2 gene (or segment thereof).

Compounds that are found to have an effect on the Aβ Arctic peptide expression, or to promote or inhibit any of the diverse biochemical effects of Aβ Arctic peptides and/or aggregated forms of Aβ Arctic peptides such as Aβ protofibrils, are then further tested and used in treatment of AD and/or related neurological disorders.

In accordance with another aspect of the invention, the transgenic animal or its progeny can be used as starting points for rational drug design to provide ligands, therapeutic drugs or other types of small chemical molecules as well as proteins, antibodies or natural products. Alternatively, small molecules or other compounds as previously described and identified by the above-described screening assays can serve as "lead compounds" in rational drug design.

EXAMPLES

General Methods

Figure 2:
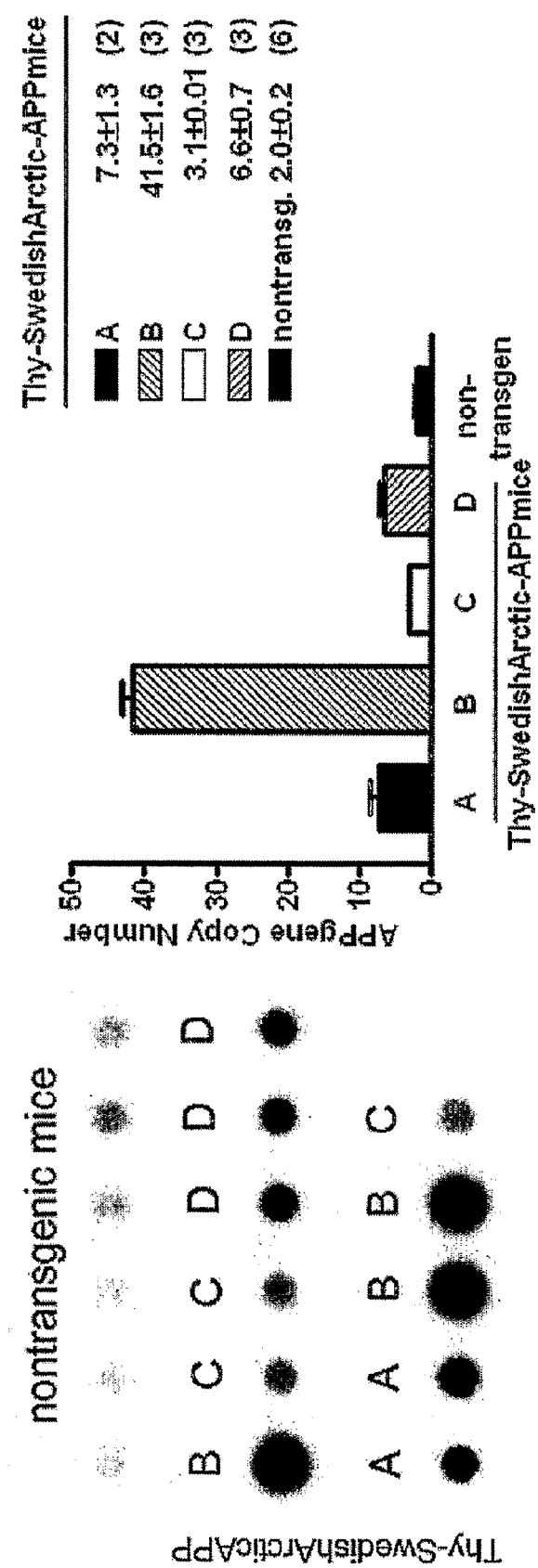
FIG. 2: Slot-blot phosphor-imager screen reflecting radioactive emission from cRNA-probes hybridized to genomic DNA samples from individual mice from the different founder lines (Thy-SwedishArcticAPP line A, B, C and D) and nontransgenic mice, as denoted for each individual mouse above the corresponding photographic signal (left) and quantitative estimates of these signals to measure copy number for the different founder lines of Thy-SwedishArctic-APPmice (right)

Standard molecular biology techniques known in the art and not specifically described were generally followed as in Sambrook et al., Molecular Cloning: A Laboratory Manual, Cold Springs Harbor Laboratory, New York (1989, 1992), and in Ausubel et al., Current Protocols in Molecular Biology, John Wiley and Sons, Baltimore, Md. (1989). Standard transgenic techniques for introduction of a foreign gene into fertilized eggs from mouse known in the art and not specifically described were generally followed as in Nagy et al., Manipulating the Mouse Embryo: A laboratory manual, Cold Springs Harbor Laboratory, New York (1986, 1994, 2002), ISBN 0-87969-574-9. (FIGS. 1 and 2). General methods in immunohistochemistry: Standard methods known in the art and not specifically described were generally followed as in Stites et al. (eds), Basic and Clinical Immunology (8th Edition), Appleton & Lange, Norwalk, Conn. (1994) and Johnstone & Thorpe, Immunochemistry in Practice, Blackwell Scientific Publications, Oxford, 1982 (FIGS. 4-5, 7-8 and 10).

Subcloning of Expression Vectors Thy-SweArcAPP

The transgenic constructs used for this study contain the murine Thy-1 expression vector and human APP cDNAs. The APP695 isoform, which is predominant APP isoform in the brain, was used. Modifications in human APP cDNA clone (Kang et al., 1987) between NruI(+145 nt) and SmaI(+3100) was made with enzymatic primer extension using the Transformer mutagenesis kit (Clontech). The following primers were used: CACTCGGTGCCCCGCGC<u>GC</u>GG<u>C</u>CGC-<u>C</u>ATGCTGCCCGGTTTGGC (SEQ ID NO: 2) and CAT-AAATAAATTAAATAAAATAACC<u>G</u>CGG<u>CC</u>GCAGAAA-CATACAAGCTGTCAG (SEQ ID NO: 3) to incorporate flanking NotI-sites and a Kozak sequence for improved initiation of translation. CAAATATCAAGACGGAGGAGAT<u>A</u>TCTGAAGTGAA<u>TC</u>TGGATGCAGAATTCCGAC (SEQ ID NO: 4) to introduce the KM670/671NL mutation and CAAAAATTGGTGTTCTTTGCAG<u>G</u>AGATGTGGGTTC-AAACAAAG (SEQ ID NO: 5) to introduce the E693G mutation. Clones were initially selected through PCR followed by restriction enzyme digestion and the selected clones were checked by DNA sequencing throughout the whole coding region of the amyloid precursor protein (APP). Correct clones were finally digested with NotI, blunt-end ligated into the XhoI-site of the Thy1 expression cassette. The construct DNA was linearized with NotI as to allow the back-bone vector sequences to be removed from the expression cassette. After purification from β-agarose gel (SeaPlaque GTG) with β-agarase (Invitrogen) and phenol-chloroform extraction the linearized DNA construct (2 µg/ml) was microinjected into pronuclear oocytes of hybrid mouse line B6-CBA-F1 (B&M, Denmark). The pronuclear microinjection technique is preferred. Transcription units obtained from a recombinant DNA construct of the invention were injected into pronuclei of animal embryos and the obtained founder transgenics were bred to establish the transgenic line.

Genotyping Litters

The resulting offspring were genotyped by cutting tail tips from weanlings, extracting DNA using a Qiagen DNA extraction kit and analyzed with PCR across the coding sequence of APP and the basal promoter of Thy-1 glycoprotein. Two primers pairs were designed Thy-1 Prom (GAATC-CAAGTCGGAACTCTT, SEQ ID NO: 6) together with APP-SQ6 (TGTCAGGAACGAGAAGGGCA, SEQ ID NO: 7), and also APP-SQ3 (GCCGACCGAGGACTGA-CCAC, SEQ ID NO: 8) together with APP-SQ7 (GACAC-CGATGGGTAGTGAA, SEQ ID NO: 9) (FIG. 1).

Animal Care and Brain Tissue Dissection and Handling

SwedishArcticAPP transgenic mice were anesthetized with 0.4 ml Avertin (25 mg/ml) checked for loss of spinal reflexes and then perfused intracardially with 0.9% saline-solution. The brain was prepared and cut in two hemispheres; one of them was immersed in 4% PFA (paraformaldehyde)/1×SPB (Sorensons Phosphate Buffer, 23 mM $KH_2PO_4$, 70.5 mM $Na_2HPO_4 \times 2H_2O$, 5 mM $NaN_3$, pH7.4) over night, 4° C. Thereafter the brain was sequentially transferred and immersed in 10%, 20% and 30% (weight/volume) Sucrose/0.1×SPB-solution each over night. The sucrose procedure was done to better preserve tissue morphology following freezing. The brain was kept in 30% sucrose-solution until the cryostat sections were cut (FIGS. 3-10).

Protein Analysis

Figure 6:
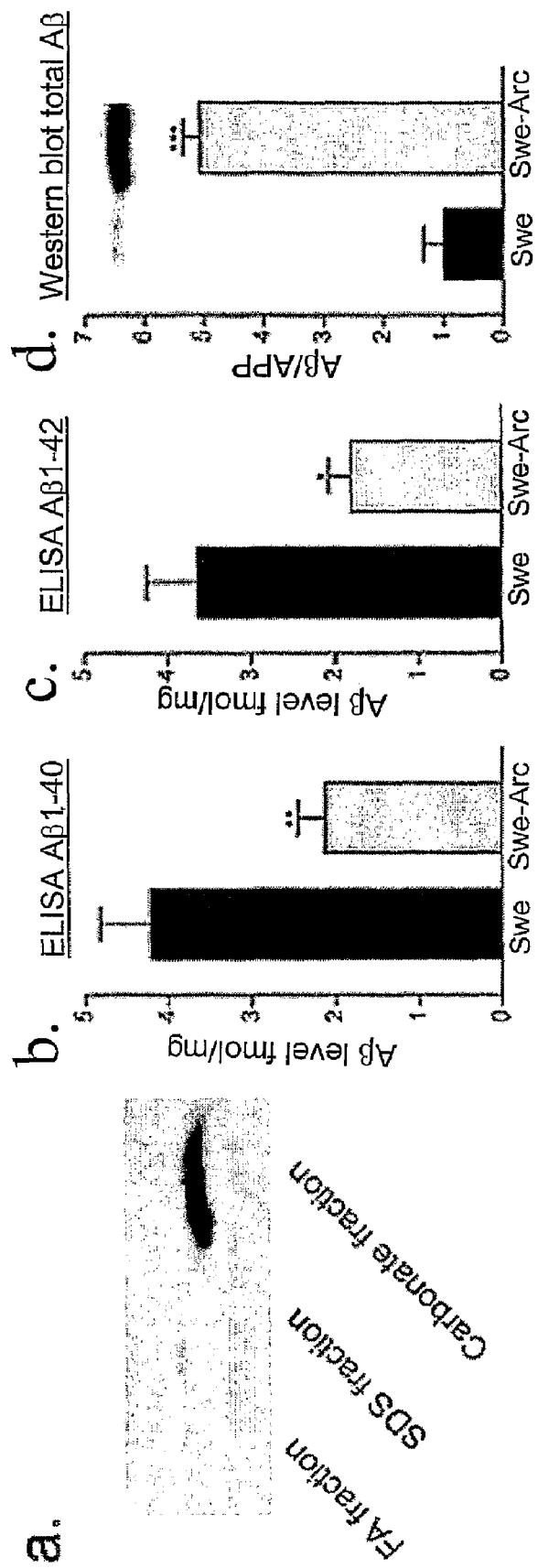
FIG. 6: Aβ protein in 2 months old Thy-SwedishArctic-APP mouse (founder line B) and Thy-Swedish-APP transgenic mouse. Sequential chemical extraction of brain tissue shows that most Aβ in Thy-SwedishArctic-APP mouse is soluble, i.e. it can be recovered by gentle chemical extraction in carbonate buffer and that little Aβ remains in the tissue upon reextraction in 1% SDS or 70% formic acid, i.e. as insoluble Aβ (a, FA=formic acid). Aβ1-40 (b) and Aβ1-42 (c) levels, as measured by ELISA, in 2 months old Thy-SwedishArctic transgenic mouse, are reduced as compared to in Thy-Swedish transgenic mouse of the same age and which expresses the same amount of the transgene (the human APP protein). In contrast, total Aβ levels, i.e. both Aβ1-40 and Aβ1-42 measured together with western blot, exhibits a five-fold increase in brain tissue from 2 months old Thy-SwedishArctic transgenic mouse as compared to Thy-Swedish transgenic mouse of the same age and which expresses the same amount of the transgene (the human APP protein) (d). The results (b-d) strongly suggest that soluble Aβ aggregates such as protofibrils are present in the brain of 2 months old Thy-SwedishArctic transgenic mouse, since western blot is a denaturing method where soluble Aβ aggregates are dissociated into their individual components, and single Aβ peptides give higher a numerical value. In contrast ELISA is non-denaturing technique, whereby each soluble Aβ aggregate will be measured as one single unit and the numerical value will be lower.

The left hemispheres of the brains were dissected from the different founder lines and weighed (FIG. 9) (as well as the other organs measured). The brain tissue was extracted in 0.2% Tween-20 in 1×PBS with protease inhibitor tablets (cat 1836153, Roche, one tablet is tablet is sufficient for 10 ml extraction solution) (FIG. 3). The extraction ratio was 1:10 (tissue weight: extraction buffer) and the tissue was extracted by 2×10 strokes on ice. The extraction solutions were centrifuged at 17900 g at 4° C. for 15 min. The supernatants were divided into aliquots and stored at −20° C. Alternatively, the brain tissues used for western blot were homogenized in 1:10 (tissue extraction volume ratio) in 100 mM $Na_2CO_3$ with 50 mM NaCl (pH11.5) with protease inhibitors, centrifuged at 100,000 g at +4° C. for 1 hr and the supernatants stored frozen at −80° C. prior to analysis. The pellet was reextracted in 2% SDS and briefly sonicated, centrifuged as previously described. The SDS-insoluble pellet was finally reextracted in 70% formic acid (FIG. 6). All samples (~40 μg protein each) were denatured by adding 1% mercaptoethanol and 1× Sample buffer (final concentration), the samples were mixed and boiled for 5 min and then loaded on 4-20% Tris-Glycine gel (InVitrogen). 1× Sample buffer contains 10% Glycerol, 2% SDS, 50 mM Tris-HCl and Bromophenol blue (diluted ×40 from a 1.5% stock). The SDS-PAGE running buffer used includes 250 mM Tris-base, 1.9M Glycine and 35 mM SDS (Sodium Dodecyl Sulfate). The gel was run at 95V. A Nitrocellulose filter was prewet in $ddH_2O$ and then equilibrated in 1× Transfer-buffer (30 mM Tris-base, 230 mM Glycine, pH8.3) with 20% methanol. The transfer set was assembled in transfer-buffer and the transfer was run at 55V, 4° C. over night. Prior to the antibody incubations the nitrocellulose-filter was boiled in 1×PBS for 5 min, to stabilize and increase the exposure of epitopes in Aβ. The filter was then blocked in freshly prepared 1% w/v nonfat dry milk, 0.1% Tween-20 in 1×TBS-buffer (100 mM Tris base, 0.9% NaCl, pH 7.5) for 1 hr at room-temperature. After blocking, the filter was incubated with primary antibody (0.5 μg/ml 6E10 or 2 μg/ml 22C11) in 0.1% Tween-20 in 1×TBS-buffer for 1 hr at room-temperature. This was followed by washing 3-4 times (5 min) in room-tempered 0.1% Tween-20 in 1×TBS-buffer. The secondary antibody, 0.2 μg/ml anti-mouseIgG/IgM-HRP (Pierce), in room-tempered 1% w/v nonfat dry milk, 0.1% Tween-20 in 1×TBS-buffer and the filter was incubated in this solution for 30 min. The filter was then washed three more times in 0.1% Tween-20 in 1×TBS-buffer, and last there was a final rinse in 1×TBS-buffer without Tween before the 5 min incubation in SuperSignal (Pierce-ECL). All incubations were let to proceed on a shaking platform. The blot filter was finally incubated against an ECL-Hyperfilm (Amersham) (FIG. 3, 6). Aβ ELISA: SDS-soluble brain tissue extracts were analyzed for Aβ1-40 and Aβ1-42 levels with ELISA using Amyloid Beta 1-40 and 1-42 ELISA kits (Signet Laboratories), according to manufacturer's instructions. To ensure equal epitope recognition between Arctic and wt Aβ by the antibodies used in the ELISA, dilution series of synthetic Aβ1-40 Arctic and Aβ1-40 wt in their monomeric form were analyzed with the Amyloid Beta 1-40 ELISA kit.

Immunohistochemistry

The brain hemispheres from the founder lines mounted on a freezing stage and 25 μm sections were cut with a sledge-microtome and stored at +4° C. until use. For the immunostaining a M.O.M. kit from Vector was utilized. The frozen fixed tissue sections were incubated in pre-heated citrate-buffer (25 mM, pH7.3) for 5 min at 85° C. This was followed by a rinse in 1×PBS. The frozen fixed tissue sections were incubated in concentrated formic acid (96%) for 5 min at RT and then rinsed in water for 10 min. After that the sections were incubated with $H_2O_2$ (0.3%) in 50% DAKO-block/50% 1×PBS for 15 min at room-temperature to block endogenous peroxidase activity. The brain sections were once again rinsed in 1×PBS before the incubation with M.O.M. Mouse IgG Blocking Reagent for 1 hr to block unspecific binding. Then the sections were permeabilized with 1×PBS (pH7.4) +0.4% Triton X-100) for 5 min and briefly rinsed twice in 1×PBS (pH7.4) to increase the surface tension. M.O.M. Mouse Diluent was used for the 5 min incubation to block unspecific binding and excess were wiped away. Incubation with 0.2 μg/ml 6E10, 14 μg/ml GFAP (clone G-A-5; 1×1500) 1.5 μg/ml Aβ42 and 1.7 μg/ml Aβ40 antibodies (primary antibodies) in MOM-diluent/0.1% Triton X-100 was let to proceed over night at +4° C. After another wash in 1×PBS buffer the sections were incubated with M.O.M. Biotinylated Anti-mouse or Anti-rabbit IgG reagent in M.O.M. Diluent/0.1% Triton X-100 for 8 min. The sections were once more rinsed in 1×PBS buffer. A 30 min long incubation with the M.O.M. kit ABC-complex (avidin-biotin-complex) were let to proceed, this was followed by a rinse in 1×PBS. Thereafter a horse radish peroxidase based substrate kit (NOVA Red, Vector) was used to develop the staining 10 min. Finally the sections were briefly washed in $ddH_2O$, dehydrated in 70%, 95%, 99.5% etOH, allowed to air-dry, dehydrated in Xylene and mounted in DPX (Dibutyl Phthalate Xylene, VWR) mounting medium for light microscopy. All the incubations above, unless stated otherwise, were carried out in room-temperature and on a shaking platform (FIGS. 4-5, 7-8 and 10). Congo Red staining was accomplished by incubating tissue sections with saturated alkaline sodium chloride solution (10 mM NaOH) for 20 min followed by Congo Red (0.2% w/v) in saturated alkaline sodium chloride solution (10 mM NaOH) for 15 min and dehydration in 70%, 95%, 99.5% etOH. Tissue sections were allowed to air-dry, dehydrated in Xylene and mounted in DPX (Dibutyl Phthalate Xylene, VWR) mounting medium for light microscopy under polarized light.

Figure 7:
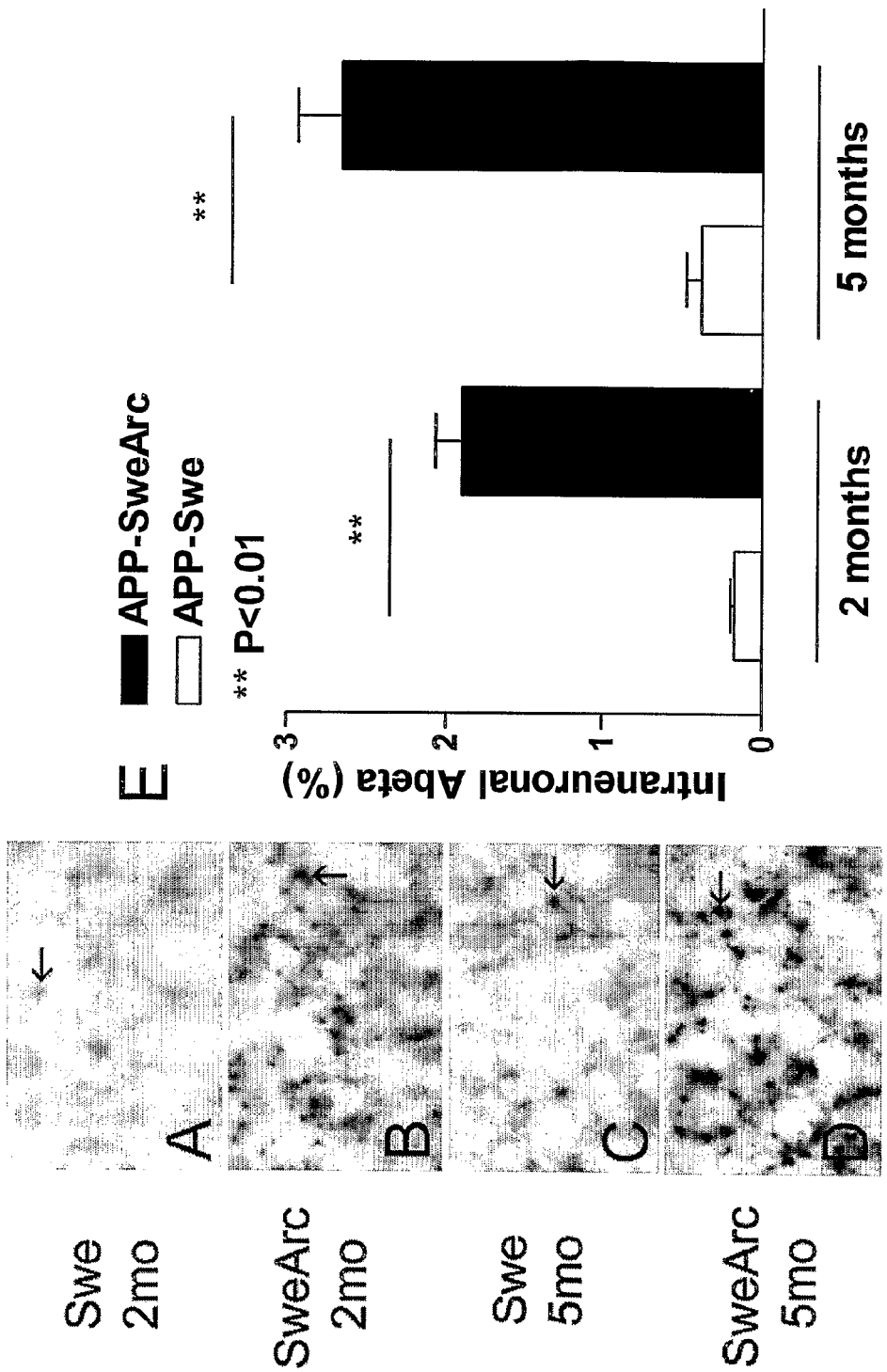
FIG. 7: Punctate intraneuronal Aβ (marked by arrows in A-D) is very strong and frequent in Thy-SwedishArctic APP at both 2 months (B) and 5 months (D) of age. In contrast, in Thy-Swedish APP (matched for transgene APP expression) intraneuronal immunostaining Aβ at both 2 months (A) and 5 months (C) of age is infrequent and faint. Quantitation image analysis (E) shows 7-fold or more increase in punctate intraneuronal Aβ immunostaining in Thy-SwedishArctic APP (solid bars) as compared to Thy-Swedish APP (open bars).
Figure 8:
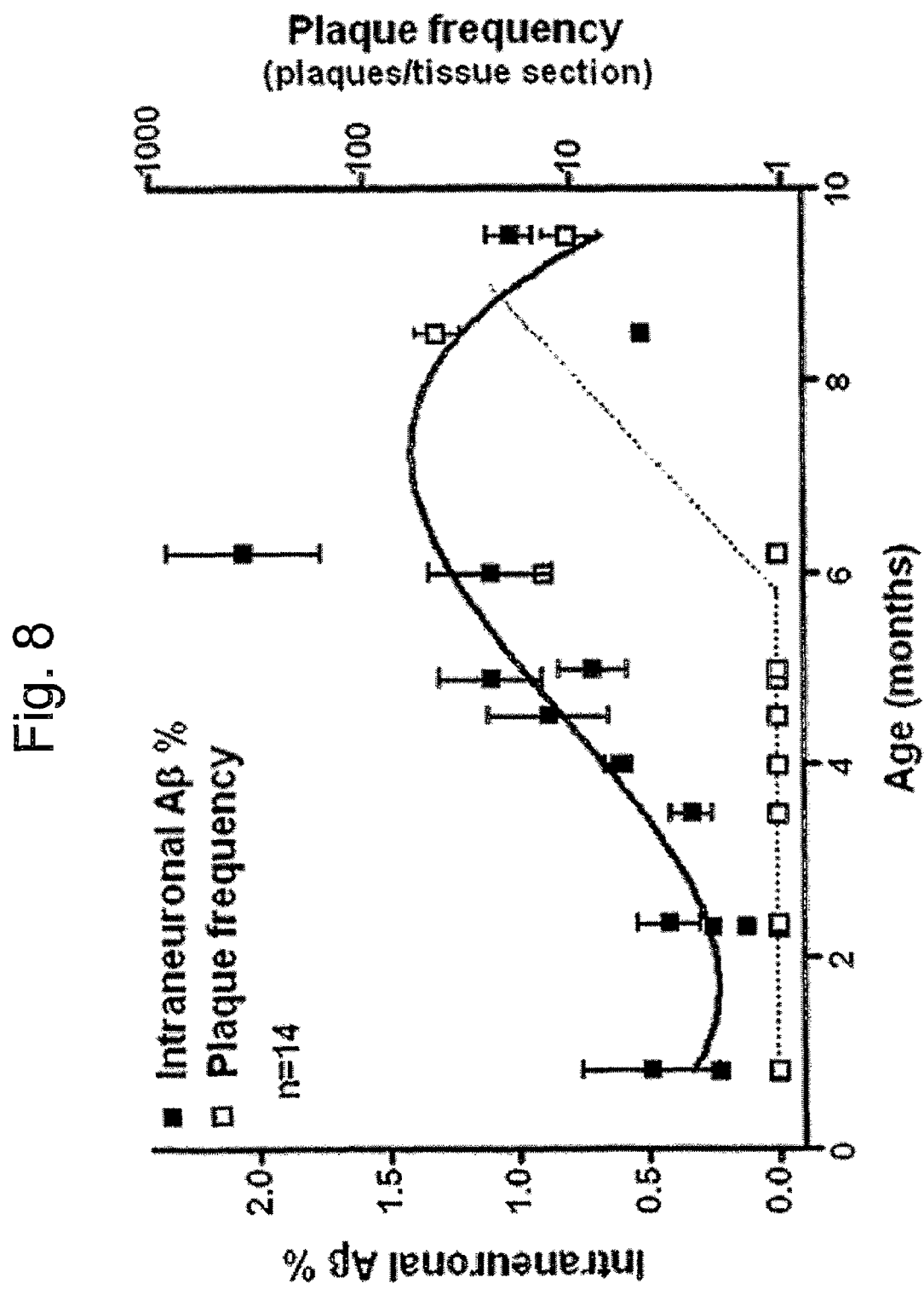
FIG. 8: Graph showing that an increase in intraneuronal Aβ aggregation predates an increase in extracellular Aβ plaque deposition by at least 2 months. Area fraction of intraneuronal Aβ aggregation in the CA1 pyramidal neurons (left y-axis) and frequency of extracellular Aβ plaque deposition in the hippocampus (right y-axis, logarithmic scale) was quantified in a cohort of Thy-SwedishArctic APP transgenic mice of various ages. Each solid square represent intraneuronal Aβ (% area fraction) from a single mouse, while the corresponding open square often located beneath represents Aβ plaque frequency in the same mouse. The results represent mean±S.E.M. of the analysis of several tissue sections from individual transgenic mice.

Image Analysis (FIGS. 7-8)

Equally spaced coronal tissue sections along the rostral-caudal axis of the hippocampus, 4-5 tissue sections from each animal, were investigated by capturing four different image fields from each separate tissue section. The images of 6E10 Aβ-immunoreactive staining were captured at 400× magnification in a Leica microscope with a cooled color CCD-camera at defined light and filter settings. The captured images of intraneuronal Aβ aggregates in the CA1 pyramidal neurons of the dorsal hippocampus were converted to grey-scale images, processed with a delineation function to sharpen edges and allow an accurate segmentation. The images were segmented with an autothreshold command (Qwin, Leica). The results are expressed as area fraction (stained $area_{tot}$/measured $area_{tot}$, expressed in %) and presented as mean±S.E.M among the tissue section analyzed from each individual transgenic mouse.

RESULTS

PCR Screening

The results from PCR genotyping are seen to the right (FIG. 1). Both sets of primers identified 4 founder mice (out of 13) having the mThy1-SwedishArctic-hAPP construct and these four founder lines were established; Thy-SwedishArcticAPP lines A-D. DNA-fragments of 428 bp lengths with upstream (A) and of 441 bp length with downstream (B) primer pairs could be detected. Offspring from each founder line were genotyped the same way (FIG. 1).

Slot Blot

Copy numbers were analyzed on individual transgene positive offspring using slot blot. The four Thy-SwedishArcticAPP founder line incorporated varying number of DNA copies, with founder line B having the highest copy number (41±2), taking into account that the nontransgenic mice have two copies of the endogenous Thy1 gene (FIG. 2).

Western Blot and ELISA

Human APP and Aβ synthesis from brain extracts of the different Thy-SwedishArctic founder lines are shown. The drawing illustrates the amyloid precursor protein (APP) and the epitopes within APP that are targeted by the antibodies. In the APP770 protein isoform, the targeted epitopes are amino acids 66-81, for 22C11, and amino acids 672-687, for 6E10. The intensity of the spots has been analyzed with the Scion Image software and relative APP overexpression in the different founder lines has been calculated. Equal loading of the gels has been confirmed with Coomassie straining and total protein analysis. The relative APP expression can be estimated with antibody 22C 11 which enables detection of both endogenous murine APP and human transgene APP. In contrast antibody 6E10 only detects human transgene APP and Aβ peptides. Thy-SwedishArcticAPP founder line B was found to display 3-fold APP-overexpression (FIG. 3). Sequential chemical extraction of brain tissue from 2 months old Thy-SwedishArctic transgenic mouse shows that most Aβ is soluble i.e. it can be recovered by gentle chemical extraction in carbonate buffer and that little Aβ remains in the tissue upon reextraction in 1% SDS or 70% formic acid i.e. as the insoluble Aβ (FIG. 6, a). Aβ1-40 (FIG. 6, b), and Aβ1-42 levels (FIG. 6, c), as measured by ELISA, in 2 months old Thy-SwedishArctic transgenic mouse are reduced as compared to Thy-Swedish transgenic mouse that are of the same age and express the same amount of the transgene (the human APP protein. In contrast total Aβ levels i.e. both Aβ1-40 and Aβ1-42 measured together with western blot is five-fold increased in brain tissues from 2 months old Thy-Swedish-Arctic transgenic mice as compared to Thy-Swedish transgenic mouse that are of the same age and express the same amount of the transgene (the human APP protein) (FIG. 6, d). The results (FIG. 6, b-d) strongly suggest that soluble Aβ aggregates such as protofibrils are present in the brain of 2 months old Thy-SwedishArctic transgenic mouse, since western blot is a denaturing method where soluble Aβ aggregates are dissociated into their individual components i.e. single Aβ peptides thereby giving higher a numerical measurement. In contrast ELISA is a non-denaturing and each soluble Aβ aggregates will be measured as one single unit and for the total number of their individual components.

Immunohistochemistry

Figure 4:
FIG. 4: APP protein in young Thy-SwedishArctic-APP transgenic mouse APP protein expression in the brain of a 1 month old Thy-SwedishArcticAPP mouse, founder line B (a—left hemisphere and b—hippocampus) and a nontransgenic mouse (c—hippocampus) stained with 6E10 (epitope 1-16 in Aβ, this antibody is specific for human APP and Aβ). The staining visualizes neuronal distribution of APP protein synthesis in the brain.
Figure 5:
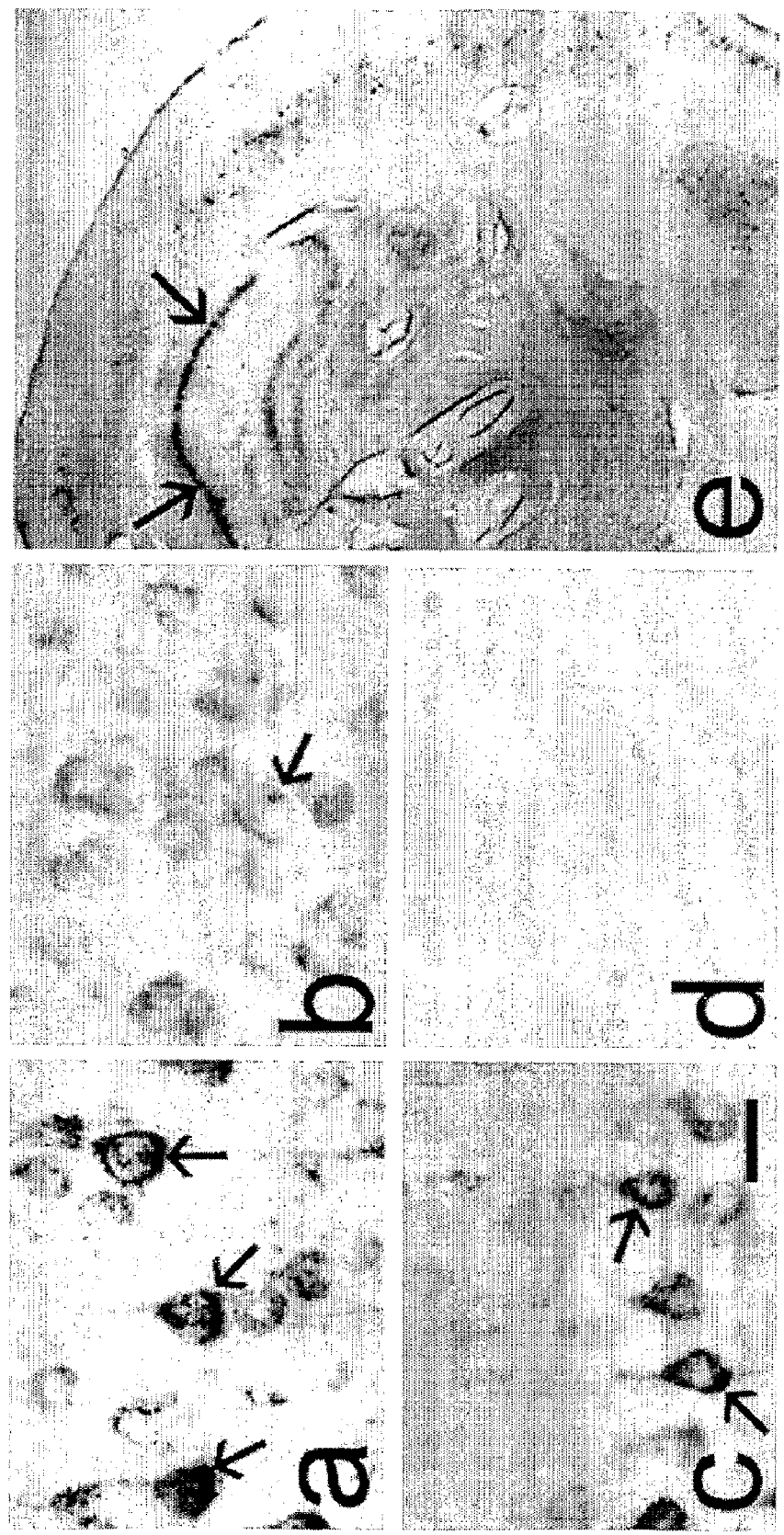
FIG. 5: Punctate intraneuronal Aβ immunostaining showing Aβ aggregation in the cerebral cortex in the Thy-SwedishArctic APP mouse (a, marked by arrows) according to the present invention and a Swedish APP transgenic mouse (b and c). The mice had equal APP expression and anatomic expression pattern (both of these parameters as well as the age of the mouse strongly influence AD phenotypes in any transgenic mouse model). Little and very faint intraneuronal Aβ was found in a 2 months old Thy-Swedish APP mouse (b). Some cortical neurons contain intraneuronal Aβ aggregates at 15 months of age in the Thy-Swedish APP transgenic mouse (c), but still much weaker and less frequent than in the Thy-SwedishArctic APP transgenic mouse at 2 months of age (a). No Aβ immunostaining was found in nontransgenic mice (d). (e) represents an overview of Aβ-aggregates in the right hemisphere of a brain of a Thy-SwedishArctic-APP transgenic mouse. The arrows points to the pronounced formic acid-resistant Aβ-immunoreactive staining in CA1 pyramidal neurons of Thy-SwedishArctic APP. Scale bar measures 20-μm (a-d).

The results from the APP immunohistochemistry are presented is seen in a one month old Thy-SwedishArcticAPP, founder line B mouse (FIG. 4, a-b), while only diffuse background staining is apparent in a nontransgenic littermate (FIG. 4, c). Punctate intraneuronal Aβ immunostaining showing Aβ aggregation in the cerebral cortex of a 2 months old Thy-SwedishArctic APP mouse (FIG. 5, a), marked by arrows). Little and very faint intraneuronal Aβ in 2 months old Thy-Swedish APP mouse with an equal APP expression (FIG. 5, b). Some cortical neurons contain intraneuronal Aβ aggregates at 15 months of age in the Thy-Swedish APP mouse (FIG. 5, c). No Aβ immunostaining was found in nontransgenic mice (FIG. 5, d). We find intraneuronal Aβ-immunopositive inclusions in the pyramidal cell layer of CA1 in the hippocampus and in scattered neurons of the lower lamina in the cerebral cortex in Thy-SweArcAPP transgenic mice (FIG. 5, e). The Aβ-immunopositive staining is resistant to pre-treatment with concentrated formic acid, which is a typical characteristic of amyloid i.e. Aβ aggregates with a β-sheet structure. Scale bar measures 20-μm (FIG. 5, a-d). Punctate intraneuronal Aβ immunostaining (marked by arrows in FIG. 5, a-d) showing Aβ aggregation in the hippocampus of a 2 months old (FIG. 7, b) and 5 months old (FIG. 7, d) Thy-SwedishArctic APP transgenic mouse. Little and very faint intraneuronal Aβ in 2 months old (FIG. 7, a) and 5 months old (FIG. 7, c) Thy-Swedish APP mouse with an equal APP expression. Image analysis show 1-fold (2 months; 1.9±0.16 (4) as compared to 0.17±0.02 (3); mean±S.E.M (n)) and 7-fold (5 months; 2.66±0.28 (3) as compared to 0.38±0.10 (4); mean±S.E.M (n) increase in percentage area covered by intraneuronal Aβ immunostaining in Thy-SwedishArctic APP transgenic mouse as compared to Thy-Swedish APP transgenic mouse (FIG. 7, e). Area fraction of intraneuronal AP aggregation in the CA1 pyramidal neurons (left y-axis) and frequency of extracellular Aβ plaque deposition in the hippocampus (right y-axis, logarithmic scale) was quantified in a cohort of Thy-SwedishArctic APP transgenic mice of various ages. Each solid square represent intraneuronal Aβ (% area fraction) from a single mouse, while the corresponding open square often located beneath represent Aβ plaque frequency in the same mouse. The results represent mean±S.E.M. of the analysis of several tissue sections from individual transgenic mice (FIG. 8). Extracellular senile plaques were also present in the caudal part of hippocampus of Thy-SweArcticAPP transgenic mouse at this age, as shown with Aβ42 and Aβ40 specific antibodies (FIG. 10, a-b). The Aβ-immunoreactivity was resistant to and enhanced by pre-treatment with concentrated formic acid. The arrows (in FIG. 10, a-b) points to Aβ-immunoreactive deposits which are displayed at higher magnification (middle images adjacent to 10, a and b). Combined Congo Red and GFAP-immunostaining shows robust astrogliotic reaction surrounding a compact amyloid plaque (FIG. 10, c), which display classical gold-green birefringence in polarized light (FIG. 10, d).

Brain Weight

Figure 9:
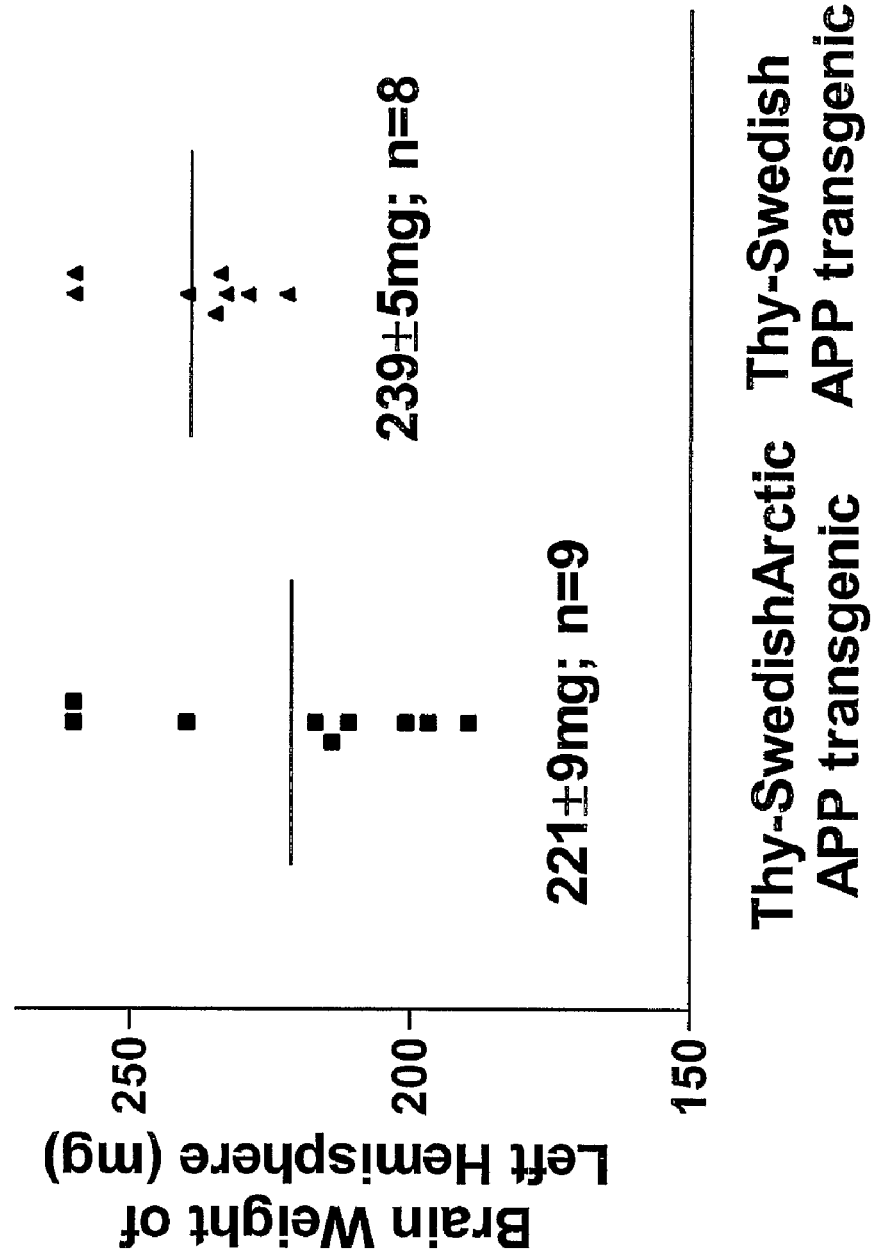
FIG. 9: Scattergram showing the group mean (line) and distribution among individuals of left hemisphere brain weight as dissected from cohorts of Thy-SwedishArcticAPP and Thy-SwedishAPP transgenic mice at 2 months of age. Thy-SwedishArcticAPP transgenic mice display reduced brain weight (221±9 mg; n=9), as compared to Thy-SwedishAPP transgenic mice (239±5 mg; n=8), which suggests atrophic changes in the brains of Thy-SwedishArctic APP transgenic mice, as is normally observed in human brain afflicted by AD pathogenesis.

The brains were dissected and divided into its two hemispheres. Scattergram showing mean and distribution among individuals of left hemisphere brain weight. The brain tissue was later biochemically analysed for human APP and Aβ synthesis. The left hemisphere was initially weighed on a balance, to serve as a measure of atrophic degeneration of the brain (FIG. 9).

REFERENCES

Cai et al., Science 259, 514-516 (1993)
Cairns et al., Neurosci Lett. 149, 137-40 (1993).
Chartier-Harlan, et al., Nature 353, 844-846 (1991)
Chishti et al., J Biol Chem. 276, 21562-21570 (2001)
Citron, et al., Nature 360, 672-674 (1992).
Corder et al., Science 261, 921-3. (1993)
DeMattos et al., Proc. Natl. Acad. Sci. USA 99, 10843-10848 (2002).
Edbauer et al., Nature Cell. Biol. 5, 486-488 (2003).
Fagan et al., Neurobiol. Dis. 9, 305-318 (2002).
Games et al., Nature 373, 523-527 (1995).
Glenner and Wong, Biochem Biophys Res Commun 120, 885-890 (1984).
Goate et al., Nature 349, 704-706 (1991).
Holcomb et al., Nat. Med. 4, 97-100 (1998).
Hsiao et al., Science 274, 99-102 (1996).
Kang et al., Nature 325, 733-6. 1987)
Klyubin et al., J. Physiol 551P, C32, commun. (2003)
Lashuel et al., J. Mol Biol., 332, 795-808 (2003).
Lantos et al., Neurosci Lett. 137, 221-4 (1992).
Lorenzo and Yankner et al., Proc. Natl. Acad. Sci USA 91, 12243-12247 (1994).
Masters et. al., Proc. Natl. Acad. Sci. USA 82, 4245-4249 (1985).

Mullan et al., Nature Genet. 1, 345-347 (1992).
Murrell, et al., Science, 254, 97-99 (1991).
Nilsberth et al., Nat. Neurosci. 4, 887-893 (2001).
Nilsson et al., J. Neurosci. 21, 1444-1451 (2001).
Näslund et al., JAMA 283, 1571-1577 (2000).
Pike et al., Brain Res. 563, 311-314 (1991).
Roher et al., J Biol. Chem. Nov 26, Epub ahead of print (2003)
Scheuner et al., Nat. Med. 2, 864-870 (1996).
Selkoe, D. J., Ann. Rev. Cell Biol. 10, 373-403 (1994).
Selkoe, Annu. Rev. Neurosci. 17, 489-517 (1994).
Strittmatter et al., Proc. Natl. Acad. Sci. USA 90, 1977-81. (1993).
Sturchler-Pierrat et al., Proc. Natl. Acad. Sci. USA 94, 13287-13292 (1997).
Suzuki et al., Science 264, 1336-1340 (1994).
Teppner et al., 6$^{th}$ Internat. Conf. AD/PD, Seville, Spain, board no 52 (2003)
Walsh et al., Nature 416, 535-539 (2001).

The invention claimed is:

1. A transgenic mouse whose genome comprises at least one transgene operatively linked to a promoter effective for expression of the transgene in the brain tissue of said mouse, the transgene/transgenes comprising a DNA sequence encoding a heterologous Amyloid Precursor Protein (APP) comprising at least the Arctic mutation (E693G) and an Alzheimer's disease (AD) pathogenic mutation or a mutation affecting AD pathogenesis, resulting in increased amounts of intracellular soluble Aβ aggregates, including Aβ peptides.

2. The transgenic mouse according to claim 1, wherein said promoter is brain tissue specific.

3. The transgenic mouse according to claim 1, wherein the endogenous APP is expressed or not expressed.

4. The transgenic mouse according to claim 1, wherein said mutation affecting AD pathogenesis is a mutant apolipoprotein E, apolipoprotein J (clusterin), α1-antichymotrypsin (ACT) or biologically fragments thereof.

5. The transgenic mouse according to claim 1, wherein said AD pathogenic mutation is one of the APP mutations KM670/671 DF, KM670/671 DY, KM670/671 EF or KM670/671 EY.

6. The transgenic mouse according to claim 1, wherein said further AD pathogenic mutation is one of the APP mutations KM670/671 NL, KM670/671 NY, KM670/671 NF, KM670/671 KL, KM670/671 DL or KM670/671 EL.

7. The transgenic mouse according to claim 1, wherein the transgenic mouse expresses only one transgene which comprises only E693G and KM670/671 NL, the Arctic mutation (E693C) and the Swedish mutation (KM670/671 NL).

8. The transgenic mouse according to claim 1, additionally comprising integrated into the genome of the mouse a homologous targeting construct for at least one of the neprilysin or insulin-degrading enzyme (IDE) genes, whereby integration disrupts these genes through gene ablation (knock-out) and enhances Aβ-40 and/or Aβ-42 Arctic peptide production.

9. A method of producing the transgenic mouse according to claim 1, comprising
a) injecting into a mouse egg or embryo at least one transgene operatively linked to a promoter effective for expression of the transgene in the brain tissue of said mouse, the transgene/transgenes comprising a DNA sequence encoding a heterologous Amyloid Precursor Protein (APP) comprising at least the Arctic mutation (E693G) and an Alzheimer's disease (AD) pathogenic mutation or a mutation affecting AD pathogenesis; and
b) transferring said fertilized egg or said embryo microinjected with said at least one transgene to a female mouse so as to produce a transgenic mouse from said fertilized egg or said embryo.

10. The method according to claim 9, wherein said promoter is brain tissue specific.

11. The method according to claim 9, wherein said endogenous APP is expressed or not expressed.

12. The method of claim 9, wherein said mutation affecting AD pathogenesis is a mutant apolipoprotein E, apolipoprotein J (clusterin), α1-antichymotrypsin (ACT) or biologically fragments thereof.

13. The method according to claim 9, wherein said AD pathogenic mutation is one of the APP mutations KM670/671 DF, KM670/671 DY, KM670/671 EF or KM670/671 EY.

14. The method according to claim 9, wherein said AD pathogenic mutation is one of the APP mutations KM670/671 NL, KM670/671 NY, KM670/671 NF, KM670/671 KL, KM670/671 DL or KM670/671 EL.

15. The method according to claim 9, additionally comprising integrated into the genome of the mouse a homologous targeting construct for at least one of the neprilysin or insulin-degrading enzyme (IDE) genes, whereby integration disrupts these genes through gene ablation (knock-out) and enhances Aβ-40 and/or Aβ-42 peptide production.

16. A method of screening agents potentially useful for treating, preventing or inhibiting Alzheimer's disease, comprising:
a) administering an agent to a first transgenic mouse according to claim 1
b) observing the ability of the first transgenic mouse to form Aβ peptides; and
c) comparing the ability of the first transgenic mouse to form Aβ peptides to the ability of a second transgenic mouse according to claim 1 to form Aβ peptides, the agent not being administered to the second transgenic mouse;
wherein a decrease in Aβ formation in the first transgenic mouse indicates that the agent is potentially useful for treating, preventing or inhibiting Alzheimer's disease.

17. A method of screening for potential diagnostic agents for Alzheimer's disease, comprising:
a) administering an agent to a first transgenic mouse according to claim 1 an agent;
b) observing the ability of the first transgenic mouse to form Aβ peptides; and
c) comparing the ability of the first transgenic mouse to form Aβ peptides to the ability of a second transgenic mouse according to claim 1 to form Aβ peptides, the agent not being administered to the second transgenic mouse;
wherein a decrease in Aβ formation in the first transgenic mouse indicates that the agent is potentially a diagnostic agent for Alzheimer's disease.

18. The transgenic mouse according to claim 6, wherein said AD pathogenic mutation is KM670/671 NL.

19. The method according to claim 14, wherein said AD pathogenic mutation is KM670/671 NL.

* * * * *